United States Patent [19]

Yamahira et al.

[11] Patent Number: 4,880,796
[45] Date of Patent: Nov. 14, 1989

[54] ANTIMICROBIAL PREPARATION

[75] Inventors: Yoshiya Yamahira, Ibaraki; Yoshiko Okuzawa, Nishinomiya; Keiji Fujioka; Shigeji Sato, both of Ibaraki; Reimei Ishikawa, Sakado, all of Japan

[73] Assignees: Sumitomo Chemical Company, Limited, Osaka; Yamanouchi Pharmaceutical Co., Ltd., Tokyo, both of Japan

[21] Appl. No.: 36,201

[22] Filed: Apr. 9, 1987

Related U.S. Application Data

[63] Continuation of Ser. No. 732,809, May 10, 1985, abandoned, which is a continuation of Ser. No. 525,258, Aug. 22, 1983, abandoned, which is a continuation of Ser. No. 305,710, Sep. 25, 1981, abandoned.

[30] Foreign Application Priority Data

Oct. 1, 1980 [JP] Japan .................................. 55-137939

[51] Int. Cl.$^4$ ............................................ A61K 31/545
[52] U.S. Cl. ........................................ 514/206; 514/970
[58] Field of Search ............................................ 514/206

[56] References Cited

U.S. PATENT DOCUMENTS

| | | | |
|---|---|---|---|
| 3,846,417 | 11/1974 | Atwal et al. | 544/28 |
| 3,856,785 | 12/1974 | Breuer | 544/28 |
| 3,923,797 | 12/1975 | Wiei | 544/24 |
| 4,084,049 | 4/1978 | Kamiya et al. | 544/16 |
| 4,150,223 | 4/1979 | Christensen et al. | 544/16 |
| 4,160,087 | 7/1979 | Yamada et al. | 544/28 |
| 4,390,535 | 6/1983 | Yamada et al. | 514/206 |

OTHER PUBLICATIONS

*Remington Pharmaceutical Sciences*, 16, p. 1367 (1980).
*Drugs of the Future*, vol. 5(5), pp. 254–255 (1980).
*The Merck Index*, 9th ed., pp. 142–143 and 1109 (1976).
Pharmazie, 24, 155–157 (1969) W/Abstract [Ring Doc. Profile (Derwent Co.)].

*Primary Examiner*—Douglas W. Robinson
*Assistant Examiner*—Raymond J. Henley, III
*Attorney, Agent, or Firm*—Stevens, Davis, Miller & Mosher

[57] ABSTRACT

An antimicrobial preparation of D-7-[α-(4-hydrooxy-6-methylnicotinamido)-4-hydroxyphenylacetamido]-3-(1-methyltetrazol-5-yl)thiomethyl-Δ$^3$-cephem-4-sodium carboxylate (hereinafter referred to as "Compound A" of enhanced stability is disclosed, which comprises a microbially effective amount of Compund A and a stabilizer selected from the class consisting of benzoic acid, sodium benzoate and nicotinamide.

6 Claims, No Drawings

ANTIMICROBIAL PREPARATION

This application is a continuation of application Ser. No. 732,809, filed May 10, 1985, now abandoned, which in turn is a continuation of application Ser. No. 525,258, filed Aug. 22, 1983, now abandoned, which in turn is a continuation of application Ser. No. 305,710, filed Sept. 25, 1981, now abandoned.

The present invention relates to an antimicrobial preparation. More particularly, it pertains to an improved antimicrobial preparation of D-7-[$\alpha$-4-hydroxy-6-methylnicotinamido)-4-hydroxyphenylacetamido]-3-(1-methyltetrazol-5-yl)thiomethyl-$\Delta^3$-cephem-4-sodium carboxylate (hereinafter referred to as "Compound A"), and to a process for producing the said antimicrobial preparation.

Compound A has recently been developed and known as an antimicrobial agent.

For administration of Compound A by injection, an injectable solution of the compound is usually freshly prepared by dissolving powdered or freeze-dried Compound A in a suitable solution such as injectable, distilled water. It has been found, however, that Compound A is unstable even in the freeze-dried form, and that it loses antimicrobial potency upon storage at room temperature for a long period of time or under severe conditions.

In order to improve the stability of the antimicrobial preparation of Compound A, we have intensively studied and found that an improved antimicrobial preparation of Compound A having an increased stability can be obtained by freeze-drying an injectable aqueous solution of Compound A to which benzoic acid, sodium benzoate or nicotinamide has been added.

Thus, the present invention provides a method for enhancing the stability of the antimicrobial preparation of Compound A. It also provides an improved antimicrobial preparation of Compound A with an enhanced stability, and a process for producing the said preparation According to the present invention, the improved antimicrobial preparation of Compound A can be prepared by freeze-drying an injectable aqueous solution of Compound A to which a stabilizer selected from the class consisting of benzoic acid, sodium benzoate or nicotinamide has been added.

The amount of the stabilizer is not particularly limited, but it can be said that 50–200 mg per 1 g potency unit of Compound A is a desirable range when the stabilizing effects, pharmacological properties, etc., thereof are taken into account.

The term "1 g potency unit" used herein means a unit amount which is equivalent to 1 g of the pure free carboxylic acid form of Compound A in exerting antimicrobial activity against B. Subtilis ATCC 6633. Usually, 0.5–2 g potency units of Compound A is administered by injection to an adult person one to several times a day. The pH value of the aqueous solution of Compound A to be freeze-dried may be in the range from pH 6 to pH 9, preferably about pH 6.5 to about pH 8.5. For the adjustment of the pH phosphates such as sodium phosphate or sodium hydrogenphosphate, or a pharmaceutically acceptable buffer solution such as phosphate buffer solution may be used, and sodium hydroxide or hydrochloric acid may also be used for a further slight adjustment.

The concentration of Compound A in the aqueous solution to be freeze-dried may vary over fairly wide limits. However, a 10 w/v %–20 w/v % of the aqueous solution of Compound A is convenient and practical to use.

The freeze-drying process per se is carried out with conventional techniques.

The improved preparation of the present invention has a remarkably increased stability compared with a conventional preparation of Compound A, as shown in Example 1 below.

The following examples are given to illustrate the present invention more precisely, but it is to be understood that they are not intended to limit the present invention.

EXAMPLE 1

Compound A (1 g potency unit) was mixed with each of sodium benzoate, nicotinamide, sodium salt of EDTA, and sodium thiosulfate in the amounts indicated in the Table below, and each of the resulting mixtures and Compound A (1 g potency unit) alone were dissolved in each of several 0.1 mM phosphate buffer solutions, which were then adjusted to pH 7.5 with a small amount of sodium hydroxide and hydrochloric acid.

After sterilizing the solutions by passing them through a bacterial filter, the solutions were poured into each of several vials (25 ml in volume) and freeze-dried.

The thus obtained freeze-dried preparations of Compound A were kept at 50° C. for 4 weeks or 12 weeks, and the residual amounts of Compound A in the preparations were measured. The results are given in the following Table.

TABLE

| Stabilizer (amount) | Residual amount of Compound A (%) | | |
|---|---|---|---|
| | At the beginning | After 4 weeks | After 12 weeks |
| Sodium benzoate (200 mg) | 100 | 96 | 90 |
| Sodium benzoate (100 mg) | 100 | 96 | 91 |
| Sodium benzoate (75 mg) | 100 | 95 | 89 |
| Sodium benzoate (50 mg) | 100 | 95 | 90 |
| Sodium benzoate (25 mg) | 100 | 92 | 86 |
| Nicotinamide (100 mg) | 100 | 95 | 88 |
| None | 100 | 88 | 79 |
| Sodium salt of EDTA (2 mg) | 100 | 90 | — |
| Sodium thiosulfate (100 mg) | 100 | 88 | — |

EXAMPLE 2

Preparations of 0.5 g potency unit of Compound A were prepared in the following way:

Ten parts by g potency unit of Compound A and one part by weight of sodium benzoate were dissolved in injectable, distilled water.

The solution was adjusted to about pH 7 with small amounts of sodium hydroxide and hydrochloric acid and sterilized by passing it through a bacterial filter.

Each 4 ml of the resulting solution containing 0.5 g potency unit of Compound A was poured into each of several vials (18 ml in volume) and freeze-dried to give preparations of Compound A of enhanced stability.

EXAMPLE 3

Preparations of 1 g potency unit of Compound A were prepared in the following way:

10,000 Parts by g potency unit of Compound A, 312 parts by weight of sodium phosphate, and 1,000 parts by eight of sodium benzoate were dissolved in injectable, distilled water, and the solution was adjusted to about pH 7.5 with small amounts of sodium hydroxide and hydrochloric acid, and sterilized by passing it through a bacterial filter.

Each 8 ml of the resulting solution which contained 1 g potency unit of Compound A was poured into each of several vials (25 ml in volume) and freeze-dried to give preparations of Compound A of enhanced stability.

EXAMPLE 4

Preparations of 2 g potency unit of Compound A were prepared in the following way:

Ten parts by g potency unit of Compound A and one part by weight of nicotinamide were dissolved in injectable, distilled water. The solution was adjusted to about pH 7 with small amounts of sodium hydroxide and hydrochloric acid and sterilized by passing it through a bacterial filter.

Each 16 ml of the resulting solution containing 2 g potency unit of Compound A was poured into each of several vials (35 ml in volume) and freeze-dried to give preparations of Compound A of enhanced stability.

EXAMPLE 5

Preparations of 1 g potency unit of Compound A were prepared in the following way:

1,000 Parts by g potency unit of Compound A, 10 parts by weight of sodium phosphate, 48 parts by weight of sodium hydrogenphosphate, and 75 parts by weight of sodium benzoate were dissolved in injectable, distilled water. The solution was adjusted to pH 7 with small amounts of sodium hydroxide and hydrochloric acid and sterilized by passing it through a bacterial filter.

Each 8 ml of the resulting solution containing 1 g potency unit of Compound A was poured into each of several vials (25 ml in volume) and freeze-dried to give preparations of Compound A (1 g potency unit) of enhanced stability.

EXAMPLE 6

Preparations of 1 g potency unit of Compound A were prepared in the following way:

Twenty parts by g potency unit of Compound A, one part by weight of sodium hydrogenphosphate, and one part by weight of benzoic acid were dissolved in injectable, distilled water. The solution was adjusted to about pH 8 with 0.2N NaOH aqueous solution, and sterilized by passing it through a bacterial filter.

Each 8 ml of the resulting solution containing 1 g potency unit of Compound A was poured into each of several vials (25 ml in volume), and freeze-dried to give preparations of Compound A of enhanced activity.

What is claimed is:

1. A solid preparation for injection use which comprises an antimicrobially effective amount of compound A which is D-7-[α-(4-hydroxy-6-methylnicotinamido)-4-hydroxyphenylacetamido]-3-(1-methyltetrazol-5-yl)thiomethyl-$\Delta^3$-cephem-4-sodium carboxylate and from 50 to 200 mg. per 1 gm. potency unit of D-7-[α-(4-hydroxy-6-methyl-nicotinamido)-4-hydroxyphenylacetamido]-3-(1-methyltetrazol-5-yl)thiomethyl-$\Delta^3$-cephem-4-sodium carboxylate of a stabilizer selected from the group consisting of benzoic acid and sodium benzoate, and a suitable amount of a pharmaceutically acceptable pH-adjustable compound in an amount sufficient to adjust pH of an injectable aqueous solution to a range of 6 to 9 when said solid preparation is reconstituted as an injectable aqueous solution prior to the injection, formed by the steps of:
   (a) forming an aqueous solution of compound A, said stabilizer and said pH-adjustable compound; and
   (b) freeze-drying the aqueous solution to form said solid preparation.

2. The solid preparation according to claim 1, wherein the concentration of D-7-[α-(4-hydroxy-6-methylnicotinamido)-4-hydroxyphenylacetamido]-3-(1-methyltetrazol-5-yl)thiomethyl-$\Delta^3$-cephem-4-sodium carboxylate in the aqueous solution to be freeze-dried is 10 w/v %–20 w/v %.

3. The solid preparation according to claim 1, wherein the stabilizer is sodium benzoate.

4. A process for producing an antimicrobial preparation of enhanced stability which comprises dissolving a microbially effective amount of D-7-[α-(4-hydroxy-6-methylnicotinamido)-4-hydroxyphenylamido]-3-(1-methyltetrazol-5-yl)thiomethyl-$\Delta^3$-cephem-4-sodium carboxylate and from 50 to 200 mg. per 1 gm. potency unit of D-7-[α-(4-hydroxy-6-methyl-nicotinamido)-4-hydroxyphenylacetamido]-3-(1-methyltetrazol-5-yl)thiomethyl-$\Delta^3$-cephem-4-sodium carboxylate of a stabilizer selected from the group consisting of benzoic acid and sodium benzoate in an aqueous injectable solution adjusting the pH value of the solution to a pH in the range of 6 to 9, sterilizing the solution by passing it through a bacterial filter and freeze-drying the solution.

5. The process according to claim 4, wherein the stabilizer is sodium benzoate.

6. The process according to claim 4, wherein the concentration of D-7-[α-(-hydroxy-6-methyl-nicotinamido)-4-hydroxyphenylacetamido]-3-(1-methyltetrazol-5-yl)thiomethyl-$\Delta^3$-cephem-4-sodium carboxylate in the aqueous solution to be freeze-dried is 10 w/v %–20 w/v %.

* * * * *